(12) United States Patent
Vidal et al.

(10) Patent No.: US 7,645,895 B2
(45) Date of Patent: Jan. 12, 2010

(54) REAGENT AND METHOD FOR PREPARING A FLUORINATED AND SILYLATED DERIVATIVE

(75) Inventors: Thierry Vidal, Lyons (FR); Nicolas Roques, Gaillac (FR); Laurent Saint-Jalmes, Vourles (FR)

(73) Assignee: Rhodia Chimie, Aubervilliers (FR)

( * ) Notice: Subject to any disclaimer, the term of this patent is extended or adjusted under 35 U.S.C. 154(b) by 199 days.

(21) Appl. No.: 10/580,787

(22) PCT Filed: Nov. 29, 2004

(86) PCT No.: PCT/FR2004/003053

§ 371 (c)(1),
(2), (4) Date: Mar. 5, 2007

(87) PCT Pub. No.: WO2005/054255

PCT Pub. Date: Jun. 16, 2005

(65) Prior Publication Data

US 2007/0276149 A1    Nov. 29, 2007

(30) Foreign Application Priority Data

Nov. 28, 2003  (FR) .................................. 03 14002

(51) Int. Cl.
*C07F 7/04*        (2006.01)
(52) U.S. Cl. ..................................... 556/478
(58) Field of Classification Search .................. 556/478
See application file for complete search history.

(56) References Cited

U.S. PATENT DOCUMENTS 5,347,058 A * 9/1994 Farnham ..................... 570/142
5,948,928 A * 9/1999 Siegele et al. ............... 556/442
6,203,721 B1 * 3/2001 Roques et al. .......... 252/183.13
6,207,847 B1 * 3/2001 Nugent, Jr. .................. 556/470

FOREIGN PATENT DOCUMENTS

| EP | 0 411 666 | 2/1991 |
|---|---|---|
| WO | WO 95/15936 | 6/1995 |
| WO | WO 98/22435 | 5/1998 |
| WO | WO 99/02535 | 1/1999 |
| WO | WO 00/60139 | 10/2000 |

OTHER PUBLICATIONS

International Search Report dated Jul. 6, 2005 issued in PCT/FR2004/003053.
Laganis et al., "Metal Silanolates: Organic Solubles Equivalents for 0-2" Tetrahedron Letters, vol. 25, No. 51, pp. 5831-5834, 1984.
Fujii et al., "Studies on Peptides, CLII. Hard Acid Deprotecting Procedure for Peptide Synthesis", Chem. Pharm. Bull., vol. 35, No. 8, pp. 3447-3452, 1987.
Margolis et al., "A Silicon-29 NMR Study of Adduct Formation in Organosilanes", Synthesis and Reactivity in Organic and Metal-Organic Chemistry, vol. 33, pp. 359-367, 2003.
Takano et al., "Desulfation of Sulfated Carbohydrates Mediated by Silylated Reagents", J. Carbohydrate Chemistry, vol. 14, No. 6, pp. 885-888, 1995.

* cited by examiner

*Primary Examiner*—Peter G O'Sullivan
*Assistant Examiner*—Sudhakar Katakam
(74) *Attorney, Agent, or Firm*—Buchanan, Ingersoll & Rooney P.C.

(57) ABSTRACT

The invention relates to a method for preparing a fluorinated and silylated derivative having a bond between the bearing carbon of at least one fluorine and one silicon. This method comprises at least one step during which a derivative of formula (I) Rf—CO—O-D, in which D is selected among silylated radicals, is placed in the presence of a base. The inventive method is used for synthesizing fluorinated derivatives.

35 Claims, 1 Drawing Sheet

REAGENT AND METHOD FOR PREPARING A FLUORINATED AND SILYLATED DERIVATIVE

This application is an application under 35 U.S.C. Section 371 of International Application Number PCT/FR2004/003053 filed on Nov. 29, 2004.

The subject matter of the present invention is a process for producing a fluorinated and silylated derivative exhibiting a bond between a carbon carrying at least one fluorine and a silicon.

The invention is targeted more particularly at the synthesis of silylated derivatives, one of the carbons connected to the silicon of which carries one, advantageously two and even three fluorine atoms.

Fluoroalkylated derivatives, and especially particularly perfluoroalkylated derivatives, are expanding in the fields of pharmaceuticals and agrochemistry. These compounds are particularly difficult and expensive to prepare, except for a few specific cases.

One of the means for perfluoroalkylating is to use $Rf^-$ carbanions or to use compounds which react like carbanions.

Mention may be made, among derivatives which react like carbanions, of reagents of the Rf-Si(Me)$_3$ type. The case where Rf is $CF_3$ is referred to as "Ruppert's reagent".

These silylated derivatives are particularly difficult to obtain and require expensive sequences, which renders their industrial application virtually impossible or exorbitantly expensive. Reference is made to the syntheses described in:

$ Organic Synthesis; Coll. Index IX, 711 (synthesis using $Et_3N_3P$); and in $ J. of Fluorine Chemistry, 2001, volume 112, 123-131.

This is why one of the aims of the present invention is to provide a process which makes it possible to produce reagents of the Rf-Si≦ type, that is to say a compound exhibiting a perhalogenated fluorinated sp$^3$ atom connected directly to a silicon atom.

Another aim of the present invention is to produce Ruppert's reagent or one of its equivalents by a technique employing, on the one hand, relatively inexpensive compounds and not requiring, on the other hand, a particularly expensive sequence of stages.

Another aim of the present invention is to produce a derivative of the above type in situ, if appropriate in the nascent state (statu nascendi).

BRIEF DESCRIPTION OF THE DRAWINGS

The diagram of the arrangement used in example IV is shown in FIG. 1.

These aims and others which will become apparent subsequently are achieved by means of a process for producing a fluorinated and silylated derivative exhibiting a bond between a carbon carrying at least one fluorine and a silicon, characterized in that it comprises a stage where a derivative of formula (I) Rf-Y—O-D is brought into contact with a base, in said formula (I):

Figure 1:
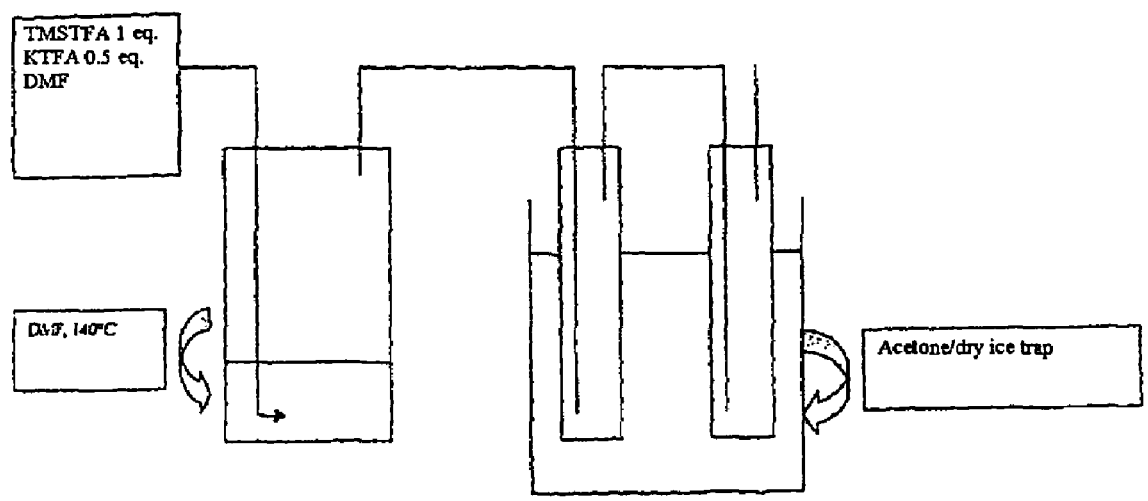

Rf represents a hydrocarbon group having from 1 to 15 carbon atoms comprising at least one fluorine atom on the carbon in the α position with respect to Y, D is chosen from silylated radicals, and where Y is chosen from carbonyl and aminoalkylene groups.

In the formula (I), Y is chosen from the carbonyl group (—CO—) and the aminoalkylene group [—(NR$_2$)C(R')—] (II), R and R' being defined below.

The aminoalkylene group is advantageously capable of resulting from the action on an amide used as solvent on an $Rf^-$, followed by a silylation (consult the PCT applications on behalf of the Applicant Company No. WO 97/19038 and No. WO 98/22435), to give a product with the structure:

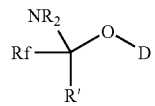

where the two R groups, which are identical or different, are such that HNR$_2$ is an optionally cyclic secondary amine advantageously of at most 10 carbon atoms and where R' is hydrogen or else an aliphatic radical (that is to say, the open bond of which is carried by an optionally functionalized sp$^3$ carbon) or aromatic radical (open bond carried by an intracyclic carbon of an aromatic ring) advantageously of at most 10 carbon atoms, preferably of at most 6.

R and R' can represent an alkyl, cycloalkyl or aryl group.

Two R groups can be connected to form a saturated or unsaturated heterocycle comprising 5 or 6 atoms.

In the context of the invention, the term "alkyl" is understood to mean a linear or branched hydrocarbon chain having from 1 to 10 carbon atoms and preferably from 1 to 4 carbon atoms.

Examples of preferred alkyl groups are in particular methyl, ethyl, propyl, isopropyl, butyl, isobutyl or t-butyl.

The term "cycloalkyl" is understood to mean a monocyclic cyclic hydrocarbon group comprising 5 or 6 carbon atoms, preferably a cyclopentyl or cyclohexyl group.

The term "aryl" is understood to mean a mono- or polycyclic aromatic group, preferably a mono- or bicyclic aromatic group comprising from 6 to 10 carbon atoms, preferably a phenyl group.

R preferably represents an alkyl group having from 1 to 4 carbon atoms, preferably a methyl group.

R' preferably represents a hydrogen atom or an alkyl group having from 1 to 4 carbon atoms, preferably a methyl group.

Advantageously, R and R' are chosen so that R'—CO—NR$_2$ is a solvent which can be used in the present invention, for example dimethylformamide or dimethylacetamide.

The preferred value of Y is the carbonyl but, as will be set out subsequently, the aminoalkylene value may occur not only directly but also as possible intermediate.

The notion of "base" should be taken into account here lato sensu since halides, such as the chloride and the fluoride, are regarded as bases in the context of the present invention. The bases for which the associated acid is stronger than trifluoroacetic acid are defined by the Hammett constant of the associated acid; the basicity of the other bases is classified and evaluated by the pKa (defined in water under standard conditions) of the associated acid. As the reaction takes place in a dry and nonaqueous medium, a base which is regarded as a weak base in an aqueous medium may have relatively high basic and nucleophilic properties in said medium. Said weak base is advantageously such that the pKa of its associated acid is at most equal to 7, advantageously to 5, preferably to 3, more preferably to 1.

The D group is a silyl group within the broad sense of the term, that is to say that it is a silicon carrying hydrocarbon radicals, that is to say comprising hydrogen and carbon, optionally connected to the silicon via an oxygen atom. Thus, D advantageously corresponds to the formula Si(R$_1$) (R$_2$) (R$_3$) (III) with R$_1$, R$_2$ and R$_3$, which are identical or different, being chosen from aryls, alkyls, alkyloxyls or halogens, preferably chlorine or fluorine. According to one implementation of the present invention, $R_1$ and $R_2$, which are identical or different, are chosen from aryls or alkyls and $R_3$ is chosen from aryls, alkyls and also from alkyloxyl radicals.

$R_1$, $R_2$ and $R_3$ advantageously represent an alkyl group of 1 to 4 carbon atoms, preferably a methyl group.

The D group is advantageously a trialkylsilyl group, preferably a trimethylsilyl group.

The base employed in the process of the invention is a weak base as defined above which is weakly silicophilic.

The base is advantageously charged, thus forming a basic anion under the operating conditions.

According to an advantageous form of the invention, this basic anion can be the carboxylate anion Rf-CO—O⁻.

If the base is silicophilic, it will react with the compound of formula Rf-CO—O-D to give the above carboxylate. Under these conditions, it is preferable in the majority of cases to directly use said carboxylate as source of base rather than a base which reacts with the silylated ester to give said carboxylate.

Consequently, according to an advantageous implementation, said basic anion is advantageously weakly silicophilic, that is to say that it is capable of forming a bond with a silyl (trimethylsilyl is taken as reference) exhibiting an energy of at most 110 kcal/mol (cf. the literature, in particular the studies by R. Walsh). It is preferable for said basic anion to be chosen from those not capable of forming a bond with a silyl or capable of forming a bond with a silyl exhibiting an energy of at most 100, preferably 90, kcal/mol.

Roughly and by way of indication, for the same nucleophilic anionic atom (such as, for example, oxygen in the various oxygen-comprising alcohols or acids), the order of the affinities may be comparable to the order of the pKa values.

In other words, it is not necessary for the base to be highly silicophilic, that is to say that it should be capable, on an intermediate basis, of breaking the bond which it forms with the silicon atom, under the operating conditions of the invention.

In practice, for this implementation, it is preferable to choose a base, or more specifically a basic anion, such that, when 1 mole of trimethylsilyl trifluoroacetate is brought into contact with $\frac{1}{10}^{th}$ of an equivalent of basic anions in anhydrous DMF, a silylated ratio (basic anion initially present–free trifluoroacetate)/(free trifluoroacetate) at least equal to $\frac{1}{50}^{th}$, advantageously to $\frac{1}{10}^{th}$, preferably to $\frac{1}{5}^{th}$, preferably to ½, is obtained at thermodynamic equilibrium. Thermodynamic equilibrium is supposedly achieved after 2 h at 25° C. The trifluoroacetate can be easily assayed in the medium by fluorine NMR (assaying of all the $CF_3COO$— entities) and potentiometry (specific assaying of the trimethylsilyl trifluoroacetate entity).

The base is advantageously non nucleophilic, so as not to react with the compound of formula (I). In other words, the base should advantageously be such as, on the one hand, unless desired, not to attack the silicon atom with ejection of the carboxylate anion, as was explained above, and, on the other hand, not to react irreversibly with the carboxylic carbon to form either an alkoxide or a carbonyl derivative with ejection of the silanolate. Thus, the base is advantageously at most as nucleophilic as a silanolate.

Mention may be made, as preferred bases, of sodium or potassium trifluoroacetate.

The amount of base to be introduced is critical only insofar as the latter, under the operating conditions, is unstable, in particular if it reacts with a derivative of formula (I) and consumes it; in this case, it is preferable to use only amounts, expressed in equivalents, which are lower than the amount of the derivative of formula (I).

The more base added, the faster the kinetics. The upper limit depends on the solubility of the base in the medium, on its strength and on its activity.

However, in general, in order to have a certain effectiveness, it is preferable for the molar ratio (B/DI) of the base, expressed in equivalents, (numerator) to the derivative of formula (I), expressed in equivalents, to be at least 0.005, advantageously 0.01, preferably 0.02.

An upper value is even less critical, in particular when, as will be seen subsequently, it is arranged for the residence time of the compounds formed to be low.

However, it may be indicated that, in general, the molar ratio (B/DI) of the base, expressed in equivalents, to the derivative of formula (I), expressed in equivalents, is at most equal to 2, preferably to 1, advantageously to 0.5, more preferably to 0.2. These upper values are advantageous in particular when the base is relatively unstable. This can in particular be the case in the context of certain carboxylates.

The reaction is advantageously carried out in an aprotic medium or solvent. Said aprotic solvent or medium advantageously comprises a concentration of acid(s) with a pKa of less than 20, advantageously than 25, preferably than 30, of at most equal to 1000 ppm in moles with respect to the moles of solvent(s). This is because these acid media react with the fluorinated and silylated carbon derivative desired, destroying it. A concentration of water or of acid as defined above significantly lowers the yield.

The medium or solvent can be either a polar aprotic solvent, advantageously an aliphatic solvent, or an ionic solvent or a molten salt, or, finally, a mixture of the types which have just been specified. Nonpolar solvents can be used if the base used is soluble in such media at a concentration of at least $10^{-3}$ equivalent per liter.

In the case of the polar aprotic solvents, it is preferable for at least one of the following conditions to be met, advantageously both. It is desirable for the donor number of said solvent to be at least equal to 10, advantageously to 20; and it is also desirable for the $\epsilon$ (dielectric constant) to be at least equal to 10, advantageously to 15.

It should be remembered that, for the definition of the donor number, reference may be made to the work by Christian Reichardt, *Solvents and Solvent Effects in Organic Chemistry*, p. 19 (1988), which work gives, as definition, the negative of the enthalpy ($-\Delta H$, expressed in kilocalorie/mol) of the interaction between the solvent and antimony pentachloride in a dilute dichloromethane solution.

The boiling point of the solvents which can be used for the present invention is advantageously at least equal to the reaction temperature, which is usually greater than or equal to 100° C., advantageously greater than 120° C. The maximum reaction temperature is advantageously at most equal to 200° C. (one, preferably two, significant figures).

When dimethylformamide is used, the operating temperature is preferably between 130° C. and 170° C., more preferably from 130° C. to 150° C.

For various reasons, in particular for recycling, it is preferable for the solvents not to exhibit, in an aqueous medium, a marked basic or acidic nature. Thus, it is more practical, when the solvent or one of the constituents of the solvent has a basic nature, for the acid associated with the base to exhibit a pKa at most equal to 5, advantageously to 5.5. The optimum constraints with regard to the acidity have been set out above.

It is preferable, with the exception of the peralkylated amides, for the solvent not to exhibit a carbonyl concentrate, unless it is desired to react the reagent Rf-D with said carbonyl function group. Furthermore, generally, the carbonyl derivatives exhibiting a hydrogen in the α position are too acidic to give a good yield.

Thus, the reaction is carried out at a temperature such that the reaction, symbolized by one of the equations below, takes place.

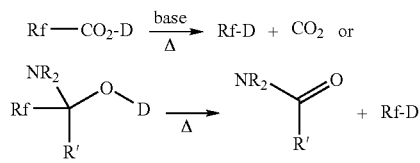

The reaction (thermolysis) temperature is usually greater than or equal to 100° C., advantageously greater than 120° C. The maximum reaction temperature is advantageously at most equal to 200° C. (one, preferably two, significant figures). The operating temperature is preferably between 130° C. and 170° C., more preferably from 130° C. to 150° C.

The pressure does not play an essential role but it can be advantageous, when the compounds are excessively volatile, in particular when the starting materials are volatile, to apply a pressure greater than atmospheric pressure.

However, in that case, it is advantageous to ensure that it is possible to remove the desired product formed from the reaction mixture as quickly as possible. This is because the high reactivity of these products, while it is highly advantageous for their properties, is a handicap during their synthesis.

In order to reduce the residence time of the desired product in the reaction mixture, it is possible either to carry out the reaction rapidly and to wait for the degree of conversion of the derivative of formula (I) to reach a value, relatively low, chosen in advance, generally between 10 and 50%, and then to separate the products and to recycle the starting material to the reaction.

Another possibility is to install a bypass on the reactor and to remove, in the circuit, the desired product as it is formed.

Finally, when the reaction products and in particular the Rf-D derivative are more volatile than the solvent, it is possible to continuously separate the desired product (Rf-D) as it is formed.

This is particularly true when Rf exhibits a number of carbons of less than 5 carbon atoms.

The solvents which have given the best result in the context of the present study are peralkylated amides, that is to say no longer carrying free hydrogen. This result is surprising insofar as such amides are known to give a reaction with Ruppert's reagent ($CF_3$—$SiMe_3$), which the present study confirms. However, this reaction does not appear to be favored at the above temperatures and this is the reason why it is preferable, when such solvents are used, to recover the desired compound (Rf-D) before allowing to cool and more preferably still to recover it as it is formed.

Mention may in particular be made, as preferred examples of solvents, of linear or cyclic carboxamides, such as N,N-dimethylacetamide (DMAC), N,N-diethylacetamide, dimethylformamide (DMF), diethylformamide or 1-methyl-2-pyrrolidinone (NMP); dimethyl sulfoxide (DMSO); or tetramethylene sulfone (sulfolane).

Another type of solvent which is satisfactory is the family of the ethers, such as, for example, ethylene glycol dimethyl ether (or glyme) or diethylene glycol dimethyl ether (or diglyme).

However, it should again be pointed out that amides, while they make possible the reaction and while they strongly promote it, exhibit the disadvantage, under certain conditions, of condensing with the reagents desired according to the present invention. Thus, Ruppert's reagent is capable of reacting with the carbonyl of dimethylformamide at relatively low temperature to give a silylated derivative of formula Rf-CH[N($CH_3$)$_2$]—O-D.

However, this reaction is reversible as the product of the addition reaction with the amide can restore the desired product on heating. During the study which has led to the present invention, the reaction below was demonstrated.

The compound of formula (I) where the Y is aminomethylene is recognized.

The term "Rf" is understood to mean the radical of formula:

where:
the X groups, which are identical or different, represent a chlorine, a fluorine or a radical of formula $C_nF_{2n+1}$ with n an integer at most equal to 5, preferably to 2, with the condition that at least one of the X groups is fluorine, fluorine advantageously carried by the carbon carrying the open bond;

p represents an integer at most equal to 2;

EWG represents an electron-withdrawing group (that is to say, the Hammett constant sigma p [$\sigma_p$] of which is greater than 0, advantageously than 0.1, preferably than 0.2), the optional functional groups of which are inert under the reaction conditions, advantageously fluorine or a perfluorinated residue of formula $C_vF_{2v+1}$, with v an integer at most equal to 8, advantageously to 5.

In the formula (IV), p is equal to 1 or 2.

The total carbon number of Rf is advantageously chosen within the closed interval (that is to say, limits included) ranging from 1 to 15, preferably from 1 to 10 and more preferably still from 1 to 4.

Advantageously, Rf corresponds to the formula:

The results are particularly advantageous when half at least of the X groups are fluorine, advantageously ¾, preferably all.

Another advantageous combination is that where half at least of the X and EWG radicals, advantageously ¾, preferably all, are chosen from fluorine atoms and perfluorinated residues of formula $C_vF_{2v+1}$ with v an integer at most equal to 8, advantageously to 5.

The intersection of the two combinations (that is to say, the subcombination corresponding to the two above constraints) corresponds to one of the preferred implementations; thus, one of the preferred implementations consists in choosing Rf from perfluorinated radicals of formula $C_vF_{2v+1}$ with v an integer chosen within the closed interval (that is to say, limits included) ranging from 1 to 15, preferably from 1 to 10. It may be opportune, in particular for reasons of ease of distillation, to choose a value for v at most equal to 8, advantageously to 5, preferably to 3.

In particular, Rf can be chosen from trifluoromethyl, pentafluoroethyl, heptafluoropropyls and nonafluorobutyls (in particular the linear version).

The Rf radical can carry at least one other functional group of the same nature (that is to say, that the sequence of atoms characteristic of the functional group, in this instance silylcarboxylate [CO—O—Si], is the same but that the substituents can be different) as that, generally identical (that is to say, carrying the same substituents) to that, which is the subject matter of the invention, so as to obtain a di- or polyfunctional compound.

In this case, EWG is or carries said functional group, namely silylcarboxylate.

When EWG is said functional group, then p is at least equal to two.

When use is made of bases which are silicophilic, the base reacts with the compound of formula (I) to give the corresponding acid salt. It is this acid salt which, at that moment, will act as base.

Thus, among the bases which can be used, use may be made of the corresponding acid salt (Rf-COO$^-$). This salt decomposes due to the strongly electron-withdrawing power of the Rf radical, which can result in side reactions and lower the conversion yield (CY, that is to say the yield of desired product with respect to substrate consumed by the reaction). On the other hand, the reaction yield (RY, that is to say the yield of desired product with respect to the amount of starting substrate introduced; RY=DC×CY) is generally fairly high.

A person skilled in the art can thus choose according to whether he desires a high reaction yield RY (yield of desired product with respect to the amount of starting substrate introduced; RY=DC×CY) or a high selectivity.

On the other hand, weaker bases which are not very silicophilic, such as, for example, heavier halides than fluorine and in particular chloride, improve the conversion yields but exhibit a lower reactivity and thus reduce the degree of conversion (DC=amount of converted product with respect to the amount of starting material), the reaction yield (RY) and also the productive output and the yield by volume.

The cocations of the bases are advantageously alkali metals, advantageously with a rank at least equal to that of sodium, or fairly large organic cations, such as oniums, in particular tetraalkylammoniums and tetraalkylphosphoniums. Use may also be made of tetraaryl-ammoniums and tetraarylphosphoniums. Use may also be made of mixed oniums, that is to say comprising both aryls and alkyls.

It should be remembered that oniums are cations, the name of which comprises an "onium" affix (generally a suffix), such as sulfonium, phosphonium, ammonium, and the like), of the tetraalkylammonium, tetraarylphosphonium or trialkylsulfonium type. These oniums are advantageously cations formed by semimetal elements of groups VB and VIB (as defined in the Periodic Table of the Elements published in the Supplement to the Société Chimique de France in January 1966) with respect to at least 4 or 3 monovalent hydrocarbon chains. It should be pointed out that the oxoniums are not very stable and cannot be used in this application. The preferred ones among these oniums are tetraalkylammoniums exhibiting from 4 to 24 carbon atoms, preferably from 4 to 12 carbon atoms, tetraalkylphosphoniums exhibiting from 4 to 24 carbon atoms, preferably from 4 to 12 carbon atoms, and tetraarylphosphoniums, as well as mixed alkyltriarylphosphoniums, dialkyldiarylphosphoniums and trialkylmonoarylphosphoniums.

It can also be advantageous to use derivatives having a highly delocalized positive charge, as in the case of Schweisinger bases, or more simply "iniums", such as, in particular, imidazoliniums or guanidiniums, and compounds used as ionic solvents or molten salts.

It should be remembered that iniums are cations, the name of which comprises an "inium" affix (generally a suffix), such as sulfinium, phosphinium, iminium, pyridinium, and the like). Preference is given to the iniums formed by semimetal elements of Groups VB and VIB (as defined in the Periodic Table of the Elements published in the Supplement to the Société Chimique de France in January 1966) with respectively 3 or 2 hydrocarbon chains, one of which is divalent and forms a double bond with said semimetal element and the others of which are monovalent. The elements from Group VB are preferred and, among the latter, nitrogen. The iniums in which the semimetal element is oxygen alone are not ordinarily stable enough to be used in the present invention.

When use is made of an ionic solvent or a molten salt, the anion or one of the anions can be chosen as base capable of giving rise to the reaction.

Mention may be made, among the preferred bases anions, of halides and in particular chloride.

Superacids do not give anions capable of acting as a base in the context of the present invention. Thus, the anions corresponding to acids having a Hammett constant in the scale of the acids of greater than 13 and even of greater than 12 are to be avoided.

The present invention can be implemented using the reaction according to the present invention to prepare in situ a reagent of the Ruppert type and thus to carry out the fluoroalkylation reaction without isolating the reagent Rf-D.

Thus, the present invention is targeted at a reagent which comprises, for successive or simultaneous addition:

a weak base which is weakly silicophilic, a compound of formula (I) with Y being a carbonyl;

a solvent, the boiling point of which is at least equal to 100° C., advantageously greater than 120° C., advantageously between 130° C. and 170° C., more preferably from 130° C. to 150° C.

In the reagent, if the base is a silanolate, the base is in an amount at least equal to one half times, advantageously one quarter times, preferably one tenth times, the molar amount of the compound formula (I).

The present invention is also targeted at the use of the above reagent for grafting an Rf to an electrophilic substrate by heating at a temperature at least equal to 120° C., advantageously between 130 and 170° C., more preferably from 130 to 150° C.

It should be mentioned that the derivative of formula Rf-C(O)—O-D can be synthesized in the reaction medium, advantageously before reaching the distillation temperature of the compound DX, by the action of the Rf-C(O)—O$^-$ anion on a compound DX where X is a halogen or pseudohalogen leaving group.

X$^-$ is advantageously chosen from the anions which form a preferred base according to the present invention, except, which goes without saying, Rf-C(O)—O$^-$. One of the leaving groups which satisfies is chlorine, as the reaction mixture is then ready to be subjected to the thermolysis which gives the desired product as it has both the anions playing a basic catalytic role and the compound of formula (I). If Rf-C(O)—O$^-$ is desired as base, it is sufficient to be positioned substoichiometrically in DX.

The following nonlimiting examples illustrate the invention.

In view of the reactivity, the volatility of the reaction products and the analytical difficulties, the yields exhibit a relatively high uncertainty.

EXAMPLE I

Qualitative Tests with Various Bases

A series of tests is carried out in which various bases are employed.

The base (1 mmol) is charged to a 60 ml Schott tube under an argon atmosphere. The DMF (2 ml) and then the trimethylsilyl trifluoroacetate (372 mg, 2 mmol) are added at 20° C. under an argon atmosphere.

The tube is closed and the reaction mixture is heated at 140° C. for the desired time.

After returning to 20° C., the reaction medium is analyzed without additional treatment.

The performances are collated in the table below.

TABLE (I)

| Base within the meaning of the description | Reaction yield (RY) CF$_3$—SiMe$_3$ % | Degree of conversion (DC) TMSTFA % | Conversion yield (CY = RY/DC) |
|---|---|---|---|
| Tetrabutylammonium fluoride | * | * | *** |
| Dimethylaminopyridine | * | *** | * |
| Tetramethylguanidine | *** | **** | ** |
| A = 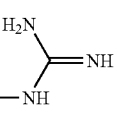 | * | **** | * |
| B = 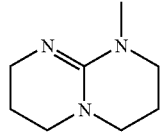 |  | ** | * |
| KCl | * |  | **** |
| Butylmethylimidazolinium chloride | * | **** | * |
| KTFA | **** | **** | **** |

\*: mediocre
\*\*: moderate
\*\*\*: good
\*\*\*\*: very good
\*\*\*\*\*: excellent

EXAMPLE II

Trimethylsilyl trifluoroacetate in the presence of potassium trifluoroacetate

Potassium trifluoroacetate (152 mg, 1 mmol) is charged to a 60 ml Schott tube under an argon atmosphere.

DMF (2 ml) and then trimethylsilyl trifluoroacetate (372 mg, 2 mmol) are added at 20° C. under an argon atmosphere.

The tube is closed and the reaction mixture is heated at 140° C. for the desired time.

After returning to 20° C., the reaction medium is analyzed without additional treatment.

The performances are collated in the table below.

EXAMPLE III

Trimethylsilyl trifluoroacetate in the presence of potassium chloride

Potassium chloride (74.5 mg, 1 mmol) is charged to a 60 ml Schott tube under an argon atmosphere.

DMF (2 ml) and then trimethylsilyl trifluoroacetate (372 mg, 2 mmol) are added at 20° C. under an argon atmosphere.

The tube is closed and the reaction mixture is heated at 140° C. for the desired time.

After returning to 20° C., the reaction medium is analyzed without additional treatment.

The performances are collated in the table below.

TABLE II

| Test | Solvent | Time (h) | Temperature (° C.) | KTFA/ TMSTFA | DC (TMSTFA)[a] (%) | RY (CF$_3$SiMe$_3$)[a] (%) | CY |
|---|---|---|---|---|---|---|---|
| 1a | DMF | 3 | 140 | 1/10 | 11 | 8 or 75[b] | / |
| 1b | DMF | 2 | 140 | 1/1 | 32 | 11 | 34 |
| 1c | DMF | 5 h 45 | 140 | 1/1 | 48 | 15 | 31 |

[a]Assaying by $^{19}$F NMR with internal standard
[b]RY = 8% with respect to the TMSTFA and RY = 75% with respect to the KTFA.

TABLE III

| Test | Solvent | Time (h) | Temperature (° C.) | KCl/ TMSTFA | DC (TMSTFA)[a] (%) | RY (CF$_3$SiMe$_3$)[a] (%) | CY |
|------|---------|----------|--------------------|-------------|--------------------|-----------------------------|----|
| 2a | DMF | 4 | 140 | 8/10 | 5 | 3 | 60 |
| 2b | DMF | 4 | 140 | 7/10 | 13 | 6 | 46 |
| 2c | PhCN[b] | 4 | 140 | 6/10 | 15 | 3.5 | 23 |

[a]Assaying by $^{19}$F NMR with internal standard
[b]Chloride source: Me$_4$NCl.

EXAMPLE IV

Trimethylsilyl trifluoroacetate in the presence of potassium trifluoroacetate (continuous addition and distillation)

A solution of potassium trifluoroacetate (1.2 g, 7.74 mmol) and of trimethylsilyl trifluoroacetate (3.09 g, 16.6 mmol) in DMF (7.1 g) is added over 2 h 40 to a DMF heel (7.13 g) heated to 140° C.

Once the addition is complete, heating is maintained for 45 minutes.

During the reaction, the volatile compounds are collected in traps cooled to −78° C.

Once heating is complete and the temperature has returned to 20° C., the various phases (recondensed volatiles and DMF) are analyzed by potentiometry and $^{19}$F NMR.

Under these conditions, the RY is 22 mol % and the DC of TMSTFA is 66 mol % (CY=33%).

The diagram of the arrangement used is given in FIG. I.

EXAMPLE V

Trimethylsilyl trifluoroacetate in the presence of potassium chloride (continuous addition and distillation)

A solution of trimethylsilyl trifluoroacetate (3.09 g, 16.6 mmol) in DMF (7.1 g) is added over 3 h 40 to a DMF heel (7.13 g), heated to 140° C., containing potassium chloride (990 mg, 13.28 mmol).

Once the addition is complete, heating is maintained for 45 minutes.

During the reaction, the volatile compounds are collected in traps cooled to −78° C.

Once heating is complete and the temperature has returned to 20° C., the various phases (recondensed volatiles and DMF) are analyzed by potentiometry and $^{19}$F NMR.

Under these conditions, the RY is 3 mol % and the DC of TMSTFA is 7 mol % (CY=43%).

The diagram of the arrangement used is identical to the above.

What is claimed is:

1. A process for producing a fluorinated and silylated derivative exhibiting a bond between a carbon carrying at least one fluorine and a silicon, comprising the step of reacting a derivative of formula (I) Rf—Y—O-D with a base, wherein in said formula (I):

Rf represents a hydrocarbon group having from 1 to 15 carbon atoms having at least one fluorine atom on the carbon in the α position with respect to Y, D is a silylated radical, and Y is a carbonyl or an aminoalkylene of formula (II) represented by —(NR$_2$)C(R')—.

2. The process as claimed in claim 1, wherein in formula II the two R groups, which are identical or different, are such that HNR$_2$ is a secondary amine of at most 10 carbon atoms and wherein R' is hydrogen or an aliphatic radical or aromatic radical of at most 10 carbon atoms.

3. The process as claimed in claim 1, wherein Y is carbonyl.

4. The process as claimed in claim 1, wherein D corresponds to the formula Si(R$_1$)(R$_2$)(R$_3$) (III) with R$_1$, R$_2$ and R$_3$, which are identical or different, being aryl, alkyl, alkyloxyl or halogen.

5. The process as claimed in claim 1, wherein D corresponds to the formula Si(R$_1$)(R$_2$)(R$_3$) (III) with R$_1$ and R$_2$, which are identical or different, being aryl or alkyl and R$_3$ being aryl, alkyl or alkyloxyl radicals.

6. The process as claimed in claim 1, wherein Rf represents a hydrocarbon group having from 1 to 10 carbon atoms.

7. The process as claimed in claim 6, wherein Rf is trifluoromethyl, pentafluoroethyl, heptafluoropropyls or nonafluorobutyls.

8. The process as claimed in claim 7, wherein Rf is trifluoromethyl.

9. The process as claimed in claim 1, wherein the base is a weak base and such that the pKa of the associated acid is at most equal to 7.

10. The process as claimed in claim 9, wherein the base is a weakly silicophilic basic anion.

11. The process as claimed in claim 10, wherein the base is such that, when 1 mole of trimethylsilyl trifluoroacetate is brought into contact with 1/10$^{th}$ of an equivalent of basic anions in anhydrous DMF, a silylated ratio (basic anion initially present-free trifluoroacetate)/(free trifluoroacetate) at least equal to 1/50$^{th}$ is obtained at thermodynamic equilibrium.

12. The process as claimed in claim 9, wherein the base presents a molar ratio, expressed in equivalents, (numerator) to the derivative of formula (I), of at least equal to 0.005.

13. The process as claimed in claim 12, wherein the molar ratio is at most equal to 2.

14. The process as claimed in claim 1, wherein the reaction is carried out in a medium selected from the group consisting of aprotic solvents, ionic solvents, molten salts and their mixture.

15. The process as claimed in claim 14, wherein the medium has a concentration of acid(s) with a pKa of less than 20, of at most equal to 1000 ppm in moles with respect to the moles of solvent(s).

16. The process as claimed in claim 14, wherein the reaction is carried out in a polar aprotic solvent, the donor number DN of which is at least equal to 10.

17. The process as claimed in claim 16, wherein the polar aprotic solvent has a dielectric constant s of at least equal to 10.

18. The process as claimed in claim 1, wherein the reaction is carried out at a at pressure at least equal to atmospheric pressure.

19. The process as claimed in claim 2, wherein in formula II two R groups, which are identical or different, are such that $HNR_2$ is a cyclic secondary amine of at most 10 carbon atoms and wherein R' is hydrogen or an aliphatic radical or aromatic radical of at most 6 carbon atoms.

20. The process as claimed in claim 4, wherein the halogen is chlorine or fluorine.

21. The process as claimed in claim 6, wherein Rf represents hydrocarbon group having from 1 to 4 carbon atoms.

22. The process as claimed in claim 9 wherein the pKa of the associated acid is at most equal to 1.

23. The process as claimed in claim 11, wherein the base is such that, when 1 mole of trimethylsilyl trifluoroacetate is brought into contact with $1/10^{th}$ of an equivalent of basic anions in anhydrous DME, a silylated ratio (basic anion initially present-free trifluoroacetate)/(free trifluoroacetate) at least equal to $1/10^{th}$ is obtained at thermodynamic equilibrium.

24. The process as claimed in claim 11, wherein the base is such that, when 1 mole of trimethylsilyl trifluoroacetate is brought into contact with $1/10^{th}$ of an equivalent of basic anions in anhydrous DMF, a silylated ratio (basic anion initially present-free trifluoroacetate)/(free trifluoroacetate) at least equal to 1/2 is obtained at thermodynamic equilibrium.

25. The process as claimed in claim 12, wherein the base presents a molar ratio, expressed in equivalents, (numerator) to the derivative of formula (I), of at least equal to 0.02.

26. The process as claimed in claim 13, wherein the molar ratio is at most equal to 0.2.

27. The process as claimed in claim 15, wherein the medium has a concentration of acid(s) with a pKa of less than 30, of at most equal to 1000 ppm in moles with respect to the moles of solvent(s).

28. The process as claimed in claim 16, wherein the reaction is carried out in a polar aprotic solvent, the donor number DN of which is at least equal to 20.

29. The process as claimed in claim 17, wherein the polar aprotic solvent has a dielectric constant $\epsilon$ of at least equal to 15.

30. The process as claimed in claim 1, wherein the base is sodium or potassium trifluoroacetate.

31. The process as claimed in claim 28, wherein the solvent is dimethylformamide.

32. The process as claimed in claim 1, wherein the reaction temperature is greater than or equal to 100° C.

33. The process as claimed in claim 32, wherein the reaction temperature is greater than 120° C.

34. The process as claimed in claim 32, wherein the reaction temperature is between 130° C. and 170° C.

35. The process as claimed in claim 32, wherein the reaction temperature is from 130° C. to 150° C.

* * * * *